US007175912B2

United States Patent
Cui et al.

(10) Patent No.: US 7,175,912 B2
(45) Date of Patent: Feb. 13, 2007

(54) SUPER-PARAMAGNETIC COMPOSITE PARTICLE WITH CORE/SHELL STRUCTURE, PREPARATION METHOD AND USE THEREOF

(75) Inventors: Yali Cui, Xian (CN); Chao Chen, Xian (CN); Qiong Wang, Xian (CN); Wenli Hui, Xian (CN)

(73) Assignee: Shanxi Lifegen Co., Ltd., Xian (CN)

( * ) Notice: Subject to any disclaimer, the term of this patent is extended or adjusted under 35 U.S.C. 154(b) by 160 days.

(21) Appl. No.: 10/833,649

(22) Filed: Apr. 28, 2004

(65) Prior Publication Data

US 2004/0219361 A1 Nov. 4, 2004

(51) Int. Cl.
*B32B 5/16* (2006.01)
(52) U.S. Cl. ...................................... 428/403; 428/701
(58) Field of Classification Search ................ 424/490, 424/618, 646, 648; 428/402, 407, 570, 701
See application file for complete search history.

(56) References Cited

U.S. PATENT DOCUMENTS

| | | | | |
|---|---|---|---|---|
| 4,450,188 A | * | 5/1984 | Kawasumi | 427/217 |
| 4,624,798 A | * | 11/1986 | Gindrup et al. | 252/62.54 |
| 4,965,007 A | * | 10/1990 | Yudelson | 252/62.53 |
| 5,262,176 A | * | 11/1993 | Palmacci et al. | 424/9.322 |
| 5,411,730 A | * | 5/1995 | Kirpotin et al. | 424/9.322 |
| 5,786,785 A | * | 7/1998 | Gindrup et al. | 342/1 |
| 5,882,802 A | * | 3/1999 | Ostolski | 428/570 |
| 5,945,158 A | * | 8/1999 | Djokic et al. | 427/216 |
| 6,344,272 B1 | * | 2/2002 | Oldenburg et al. | 428/403 |
| 6,387,498 B1 | * | 5/2002 | Coulter et al. | 428/403 |
| 6,773,823 B2 | * | 8/2004 | O'Connor et al. | 428/548 |
| 6,783,569 B2 | * | 8/2004 | Cheon et al. | 75/348 |

OTHER PUBLICATIONS

"Silver and Gold Plated Beads", Arizona Bead Company catalog page.*
Kim et al, "Surface modification of superparamagnetic nanoparticles for in-vivo bio-medical applications", Mat. Res. Soc. Symp. Proc. vol. 704, W11.2.1-WW11.2.6, 2002.*

(Continued)

*Primary Examiner*—H. Thi Le
(74) *Attorney, Agent, or Firm*—Seed IP Law Group PLLC

(57) ABSTRACT

The invention relates to a super-paramagnetic composite particle with core/shell structure, preparation method and use thereof. The composite particle is consisted of a core portion and a shell portion coated on the surface of the core portion, wherein said core portion is 10–70% by weight and said shell portion is 30–90% by weight based on the total weight of the composite particle, and said core portion is consisted of magnetic particles of $Fe_3O_4$, $\gamma$-$Fe_2O_3$ or other ferric oxides, or magnetic particles of ferrites of tervalent ferrum and bivalent manganese, nickel, zinc or copper, and the said shell portion is consisted of elementary gold or silver. The particle has an average diameter of 0.05–50 μm. The preparation method comprises preparing the core portion magnetic particle by chemical co-precipitation and depositing gold or silver to coat the magnetic particle by chemical reduction. The composite particle can label biological materials or nonbiological materials selected from the group consisted of nucleic acid, antigen, antibody, enzyme, polypeptide, polysaccharide, avidin, streptavidin or cell and the like, and be used in biological test and nonbiological test.

11 Claims, 1 Drawing Sheet

OTHER PUBLICATIONS

Guobin et al, "Surface Modification of Nano-magnetic Fe3O4 Particles and its Applications", China-EU Forum on Nanosized Technology, p. 68-76, 2002.*

Zhou et al, "Nanostructures of gold coated iron core-shell nanoparticles and the nanobands assembled under magnetic field", Eur. Phys. J. D. 16, 289-292 (2001).*

* cited by examiner

SUPER-PARAMAGNETIC COMPOSITE PARTICLE WITH CORE/SHELL STRUCTURE, PREPARATION METHOD AND USE THEREOF

CROSS REFERENCE TO RELATED APPLICATION

This application claims the benefit of Chinese Application No. 03124061.5, filed Apr. 30, 2003, which is incorporated herein by reference in its entirety.

BACKGROUND OF THE INVENTION

1. Field of the Invention

The present invention relates to a super-paramagnetic composite particle with core/shell structure, preparation method and use thereof. More particularly, the present invention related to this core/shell super-paramagnetic composite particle for labeling biological molecule and materials or non-biological molecules using the functional group consisted of nucleic acid, antigen, antibody, enzyme, polypeptide, polysaccharide, avidin, streptavidin, cell, and the like, the preparation method and the use thereof. The core/shell super-paramagnetic composite particle according to the present invention can be used in purification or detection of various biological molecules and other chemical molecules.

2. Description of the Related Art

Magnetic particles with nanometer size such as iron oxide are super-paramagnetically and magnetically responsive, which allows them to be separated repeatedly and without aggregation by manipulating magnetic field consisted of NdFeB permanent magnet. Super-paramagnetic nanoparticles coated with synthetic macromolecule, biological macromolecule and inorganic material have been widely used in biological and medical areas such as affinity chromatography, cell sorting, separation and purification of nucleic acid and protein, and targeted therapy. In addition, because mercapto labeled oligonucleotide or antibody is readily modified onto the surface of nano-gold or nano-silver, the uses of nano-gold and nano-silver in the areas of nucleic acid detection, immunoassay and the like is well known to those skilled in the art. Intensive studies regarding applying nano-gold modified with oligonucleotide probe in nucleic acid detection have been reported by Mirkin etc. (University of Northwest, USA) since 1996. The particle is used in DNA chip detection technology. CN 1339609 discloses a nano-particle labelling gene probe, the preparation method and the use thereof (Daiwen Pang et. al., Wu Han University, China). It is reported that the probe is particularly suitable for low integrated level gene chip of diagnostic type.

A $Fe_3O_4$/Au super-paramagnetic particle with core/shell structure and the mechanism of preparation has been studied (Yali Cui et. al., Preparation and mechanism of $Fe_3O_4$/Au core/shell super-paramagnetic microspheres. *Science in China* (series B) 44(4): 404–410, 2001).

BRIEF SUMMARY OF THE INVENTION

According to the present invention, one aspect provides a core/shell super-paramagnetic composite particle for labeling nucleic acid, antigen, antibody, enzyme, polypeptide, polysaccharide, avidin, or streptavidin, cell and the like, which can be practically used in surface modification of bioactive material. The present invention also provides a method for preparation of the composite particle.

Another aspect of the present invention provides the use the above composite particle as carrier or as signal to detect nucleic acid, antigen, antibody and other biomaterials.

DETAILED DESCRIPTION OF THE INVENTION

Figure 1:
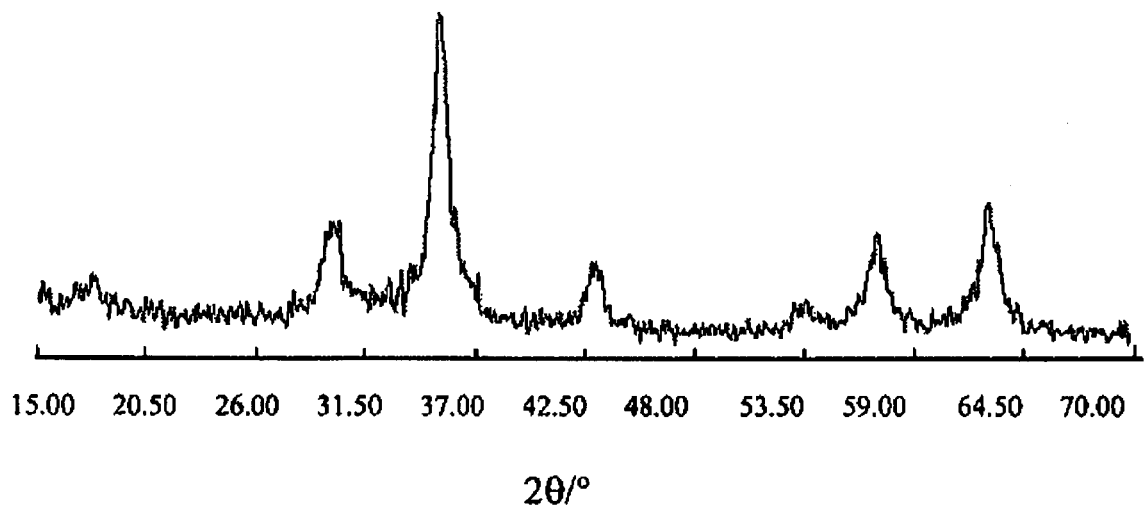
FIG. 1 shows X-ray diffraction spectrum of $Fe_3O_4$ particle.

The present invention provides a core/shell super-paramagnetic composite particle comprising a core portion and a shell portion coated on the surface of the core portion, wherein said core portion is consisted of magnetic materials, the said shell portion is consisted of noble metal materials, characterized in that said composite particle has an average diameter of 0.05–50 µm, said core portion is 10–70% by weight and said shell portion is 30–90% by weight based on the total weight of the composite particle, wherein said core portion is consisted of magnetic particles of $Fe_3O_4$, $\gamma$-$Fe_2O_3$ or other ferric oxides, or magnetic particles of ferrites composed of tervalent ferrum and bivalent manganese, nickel, zinc or copper, and said shell portion is consisted of gold or silver or other noble metals. The composite particle has good suspension stability and effective response to an external magnet in aqueous suspension solutions.

The present invention also provides a method for preparation of the composite particle. The composite particle was prepared by reduction of a noble metal salt such as $Au^{3+}$ with hydroxylamine in the presence of $Fe_3O_4$ particles as seed. In particular, the method comprises the following steps:

a. preparing a core portion magnetic particle by chemical co-precipitation or other methods, and then rinsing with water several times until the pH reached at 6~7;

b. dispersing the core particles in 0.01–1% $HAuCl_4 \cdot 4H_2O$ or other noble metal salt solution and slowly mixing with shaking to absorb $Au^{3+}$ or $Ag^+$ onto the core surface;

c. adding reducing agent to the system, continually shaking, depositing a layer of gold or silver to coat the magnetic particle by chemical reduction, forming core/shell structure of $Fe_3O_4$/Au and then washing with water to neutralize the pH of sample, wherein hydroxylamine hydrochloride or trisodium citrate is used as reducing agent.

Preferably, the method according to the present invention comprises the following steps:

a) mixing an aqueous solution of Fe (II) salt or other bivalent metal salt with an aqueous solution of Fe (III) at a ratio of 1:2–1:4 by molar with agitation, followed by adding 1–6 mol/L aqueous sodium hydroxide solution or 30% (w.t.) aqueous ammonia, adjusting the pH of the mixture to 10–13, agitating rapidly for 20–60 minutes at the room temperature, then warming to 60–70° C., and continuing incubation for 30–60 minutes with agitation, separating the precipitation of slurry state super-paramagnetic nanoparticle in average particle size of 15–30 nm from external magnetic field, washing with distilled water repeatedly until obtaining neutral magnetic nanoparticle, further diluting the magnetic nanoparticle with water to magnetic fluid of constant volume wherein the solid content is 5–20 mg/ml, then diluting it as a seed for the preparation of magnetic composite particle, the magnetic nanoparticles in water have aggregated to certain extent, thus obtaining the different sizes of composite particles;

b) to the magnetic nanoparticle suspension obtained in step a, adding 50–500 ml of a solution of Au (III) salt or Ag (I) salt at concentration of 0.01–1%, shaking for 30 minutes, allowing Au (III) or Ag (I) ion to absorb on the surface of magnetic nanoparticle sufficiently, then adding 15–40 ml of reducing agent, such as hydroxylamine hydrochloride or trisodium citrate at concentration of 40 mmol/L, reacting for 5–40 minutes, further adding 1–10 ml of a solution of Au (III) salt or Ag (I) salt at concentration of 0.01–1%, shaking for 10 minutes, coating a reduced layer of gold or silver on the surface of the magnetic nanoparticle, forming super-paramagnetic composite particles having core/shell structure, separating magnetically, washing repeatedly with distilled water.

More preferably, the surfactant such as polyethylene glycol, Triton X-100, Tween-20 etc. could be added to the reaction system of step a in order to get uniform particle dispersion. The pH of the reaction medium of step a) is controlled to about 6~7.

The core/shell super-paramagnetic composite particle according to the present invention can be used to label biological materials or nonbiological materials selected from the group consisted of nucleic acid, oligonucleotide probe, antigen, antibody, enzyme, polypeptide, polysaccharide, avidin, or streptavidin, cell and the like.

Another aspect of the present invention provides use of above core/shell super-paramagnetic composite particle for labeling biological materials or nonbiological materials selected from the group consisted of nucleic acid, oligonucleotide probe, antigen, antibody, enzyme, polypeptide, polysaccharide, avidin, streptavidin, cell and the like.

The biological materials or nonbiological materials are selected from the group consisted of nucleic acid, oligonucleotide probe, antigen, antibody, enzyme, polypeptide, polysaccharide, avidin, streptavidin, cell and the like The so-labelled core/shell super-paramagnetic composite particle according to the present invention can then be used in separation or detection of biomolecules and non-biomolecules such as nucleic acid, protein, polysaccharide and the like.

Another aspect of the present invention therefore provides use of above core/shell super-paramagnetic composite particle in biological test and nonbiological test.

The super-paramagnetic composite particle according to the present invention possesses advantages that both magnetic particles and noble metal have. The super-paramagnetic composite particle is not only readily separable under the action of magnetic field, but also very likely to bind with bioactive materials including mercapto oligonucleotide, protein, polysaccharide and the like. Therefore, it is very suitable for the separation of nucleic acid and protein, nucleic acid hybridization and detection, and antigen-antibody immunoassay and other biological system detection, particularly for the visualization detection of biochip. Because the composite particle has both super-paramagnetic of magnetic particles and characteristics of gold and silver visualization, the biological test system labelled with the particle can enrich, separate and purify reactants captured on the surface of composite particle by only one-step of simple magnetic separation, without centrifugation or other enzymatic treatment steps. Therefore, it improves the sensitivity and specificity of detection, shortens the detection time. In addition, the detection is achieved through visualization, thus it is possible to achieve detection conveniently without the confinement of expensive instruments.

EXAMPLES

The following examples are intended to further illustrate the present invention without limiting it in any way.

Example 1

The example is intended to illustrate the realizability of the preparation of the core/shell $Fe_3O_4$/Au super-paramagnetic composite particle according to the present invention.

1. The Preparation of Super-paramagnetic $Fe_3O_4$ Particle:

A mixture of $FeCl_2$/$FeCl_3$ at a molar ratio of 1:2 was added to 6 mol/L NaOH solution with agitation. After stirring the mixed solution for about 1 hour at 20° C., the temperature was raised to about 70° C. The solution was stirred for about 1 hour. With the aid of external magnetic field, resultant super-paramagnetic $Fe_3O_4$ particle was separated. The $Fe_3O_4$ particle was washed with distilled water repeatedly until obtaining neutral $Fe_3O_4$ particle. The X-ray diffraction spectrum is used to analysis the composition of the $Fe_3O_4$(FIG. 1) super-paramagnetic $Fe_3O_4$ particle in average particle size of 15–30 nm was sorted. The suspension of $Fe_3O_4$ was used as a seed for the preparation of $Fe_3O_4$/Au composite particle.

Figure 2:
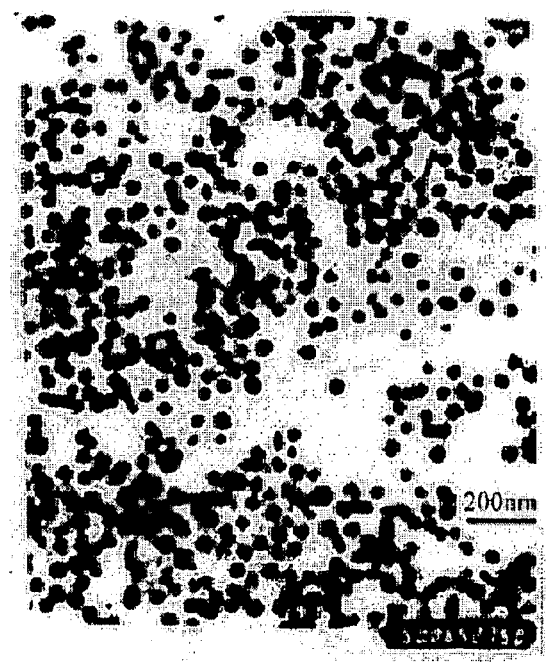
FIG. 2 shows TEM photo of $Fe_3O_4$/Au paramagnetic composite nanoparticle with 50 nm diameter.

2. The Preparation of Nanosized $Fe_3O_4$/Au Super-Paramagnetic Composite Particle with Core/shell Structure:

A 25 ml of $Fe_3O_4$ (about 1.7 mmol) suspension was separated in magnetic field for 30 minutes, after the supernatant was removed, and 120 ml aqueous $HAuCl_4$ solution at concentration of 0.1% mmol/L was added thereto. After shaking for 30 minutes, 5 ml aqueous $NH_2OH$—HCl solution at concentration of 80 mmol/L was added. 10 minutes later, 5 ml aqueous $HAuCl_4$ solution at concentration of 1% was further added. After shaking for 10 minutes, $Fe_3O_4$/Au magnetic composite particle with core/shell structure was gradually formed. The particle was magnetically separated, washed with distilled water for five times, and diluted to constant volume of 25 ml. The TEM photo for this magnetic composite particles with 50 nm diameter was shown in FIG. 2.

Example 2

The example is intended to illustrate the surface of core/shell $Fe_3O_4$/Au super-paramagnetic composite particle according to the present invention can be modified with streptavidin by conventional method.

A suspension of $Fe_3O_4$/Au magnetic composite particle was adjusted to pH of 6.0–7.0 with aqueous $K_2CO_3$ solution at concentration of 0.1 mol/L. With the agitation of electromagnetic stirrer, 1 mg of streptavidin was dissolved in 0.1 mol/L PBS with a pH of 6.0–7.0 to obtain aqueous streptavidin solution (0.02%, w/v,), then is added to the suspension of magnetic composite particle obtained in above example 1 within 5 minutes. 5% bovine serum albumin (BSA) was added as stabilizer to a final concentration of 1% with the agitation of magnetic stirrer. The mixture after reaction was separated with magnetic separator. The separated $Fe_3O_4$/Au super-paramagnetic composite particle modified with streptavidin was washed with 0.1 mol/L of PBS, and stored in 4° C. refrigerator ready for use.

Example 3

The example is intended to illustrate that the surface of core/shell super-paramagnetic composite particle according to the present invention can be coupled with oligonucleotide probe by conventional method.

5 ml of core/shell super-paramagnetic composite particle at concentration of 15 nM was mixed with —SH labeled oligonucleotide probe. The final concentration of probe was adjusted to 5 µM. After reacting for 16 hours, the mixed solution was transferred into 10 mM phosphate buffer solution (pH=7.0) containing 0.1 M NaCl and kept for 40 hours. The mixture after reaction was magnetically separated by magnetic separator, washed with 10 mM phosphate buffer solution (pH=7.0) containing 0.1 M NaCl and stored in 10 mM phosphate buffer solution (pH=7.0) containing 0.3 M NaCl.

Example 4

The example is intended to illustrate the surface of core/shell super-paramagnetic composite particle according to the present invention can be coupled with antibody by conventional method.

0.5 ml of suspension of core/shell type super-paramagnetic composite particle was magnetically separated and the supernatant was removed. 0.5 ml of Tris-HCl at concentration of 0.05 M (pH=7.6) was added. After reacting for 5 minutes, the supernatant was removed by magnetic separation. Stock solution of antibody was diluted to 0.2 mg/ml with 0.05 M Tris-HCl (pH=7.6), wherein 200 µl was then taken to add to the composite particle. After mixing homogeneously, the reaction was conducted for 30 minutes with shaking. The mixture after reaction was separated by magnetic separator, and the separated super-paramagnetic composite particle coated with antibody was washed with 0.02 M TBS (pH=8.2) and stored for ready use.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A super-paramagnetic composite particle with core/shell structure capable of labeling biological materials or nonbiological materials, comprising: a core portion and a shell portion coated on the surface of the core portion, wherein the core portion is consisted of magnetic materials, the shell portion is consisted of noble metal materials, characterized in that the composite particle has an average diameter of 0.05–50 µm, the core portion is 10–70% by weight and said shell portion is 30–90% by weight based on the total weight of the composite particle, wherein the core portion is consisted of magnetic particles selected from $Fe_3O_4$, $\gamma$-$Fe_2O_3$, bivalent manganese ferrite, bivalent nickel ferrite, bivalent zinc ferrite and bivalent copper ferrite, and the shell portion is a layer of noble metal with thickness of 0.020~20 µm.

2. The composite particle according to claim 1, having excellent stability and effective response to an external magnet in aqueous suspension solutions.

3. The composite particle according to claim 1, wherein the biological materials or non-biological materials can be immobilized on a surface of the particle via one or more functional groups on the biological or non-biological materials.

4. The composite particle according to claim 1, wherein the composite particle has an average diameter of 0.05–5 µm, and has a shell with thickness of 0.02–2 µm.

5. The composite particle according to claim 1, wherein the core portion is 15–50% by weight and said shell portion is 50–85% by weight based on the total weight of the composite particle.

6. A super-paramagnetic composite particle with core/shell structure capable of labeling biological materials or nonbiological materials, comprising:
a core portion comprising one or more magnetic particles selected from the group consisting of ferric oxides and ferrites, wherein the ferric oxide is $Fe_3O_4$ or $\gamma$-$Fe_2O_3$ and the ferrite comprises a tervalent iron; and a bivalent metal selected from the group consisting of manganese, nickel, zinc and copper; and
a shell portion coated on a surface of the core portion, the shell portion comprising a noble metal;
wherein the composite particle has an average diameter of 0.05–50 µm, the core portion is 10–70% by weight based on the total weight of the composite particle and the shell portion is 30–90% by weight based on the total weight of the composite particle.

7. The composite particle according to claim 6 wherein the noble metal is gold or silver.

8. The composite particle according to claim 6 wherein the biological or non-biological materials are selected from the group consisting of nucleic acid, antigen, antibody, enzyme, polypeptide, polysaccharide, avidin, streptavidin and a biological cell.

9. A super-paramagnetic composite particle with core/shell structure capable of labeling biological materials or nonbiological materials, comprising:
a core portion comprising one or more magnetic particles selected from the group consisting of $Fe_3O_4$, $\gamma$-$Fe_2O_3$, $MgFe_2O_4$, $NiFe_2O_4$, $ZnFe_2O_4$ and $CuFe_2O_4$; and
a shell portion coated on a surface of the core portion, the shell portion comprising a noble metal; wherein the composite particle has an average diameter of 0.05–50 µm, the core portion is 15–50% by weight based on the total weight of the composite particle, and the shell portion is 50–85% by weight based on the total weight of the composite particle.

10. The composite particle according to claim 9 wherein the noble metal is gold or silver.

11. The composite particle according to claim 9 wherein the biological or non-biological materials are selected from the group consisting of nucleic acid, antigen, antibody, enzyme, polypeptide, polysaccharide, avidin, streptavidin and a biological cell.

* * * * *